United States Patent [19]
Chou et al.

[11] Patent Number: 4,918,255
[45] Date of Patent: Apr. 17, 1990

[54] HETEROGENEOUS ISOPARAFFIN/OLEFIN ALKYLATION WITH ISOMERIZATION

[75] Inventors: Tai-Sheng Chou, Pennington, N.J.; Albin Huss, Jr., Chadds Ford; Clinton R. Kennedy, West Chester, both of Pa.; Robert S. Kurtas, Sewell, N.J.

[73] Assignee: Mobil Oil Corp., New York, N.Y.

[21] Appl. No.: 219,527

[22] Filed: Jul. 15, 1988

[51] Int. Cl.$^4$ .............................................. C07C 2/58
[52] U.S. Cl. .................................. 585/331; 585/721; 585/722; 585/726; 585/728
[58] Field of Search ............... 585/331, 722, 726, 728, 585/721

[56] References Cited

U.S. PATENT DOCUMENTS

| | | |
|---|---|---|
| 2,450,764 | 10/1948 | Meyers ............................ 585/728 |
| 2,804,491 | 8/1957 | May et al. . |
| 2,939,890 | 6/1960 | Hervert et al. . |
| 3,131,120 | 4/1964 | Chupp et al. . |
| 3,131,230 | 4/1964 | Hervert et al. . |
| 3,140,249 | 7/1964 | Plank et al. . |
| 3,140,251 | 7/1964 | Plank et al. . |
| 3,140,253 | 7/1964 | Plank et al. . |
| 3,236,671 | 2/1966 | Dybalski et al. . |
| 3,251,902 | 6/1966 | Garwood et al. . |
| 3,450,644 | 6/1969 | Lanewala et al. . |
| 3,467,728 | 9/1969 | Hervert et al. . |
| 3,549,557 | 12/1970 | Bolton et al. . |
| 3,624,173 | 11/1971 | Kirsch et al. . |
| 3,644,565 | 2/1972 | Biale et al. . |
| 3,647,916 | 3/1972 | Caesar et al. . |
| 3,655,813 | 4/1972 | Kirsch et al. . |
| 3,702,886 | 11/1972 | Argauer et al. . |
| 3,706,814 | 12/1972 | Kirsch et al. . |
| 3,738,977 | 6/1973 | Biale et al. . |
| 3,800,003 | 3/1974 | Sobel . |
| 3,855,342 | 12/1974 | Huang et al. . |
| 3,855,343 | 12/1974 | Huang et al. . |
| 3,862,258 | 1/1975 | Huang et al. . |
| 3,893,942 | 7/1975 | Yang . |
| 3,917,738 | 11/1975 | Fenske et al. . |
| 3,997,621 | 12/1976 | Brennan . |
| 4,016,218 | 4/1977 | Haag et al. . |
| 4,308,414 | 12/1981 | Madgavkar et al. . |
| 4,325,994 | 4/1982 | Kitashima et al. . |
| 4,365,105 | 12/1982 | Morganson et al. . |
| 4,374,296 | 2/1983 | Haag et al. . |
| 4,384,161 | 5/1983 | Huang . |
| 4,394,296 | 7/1983 | Madgavkar et al. . |
| 4,418,235 | 11/1983 | Haag et al. . |
| 4,429,177 | 1/1984 | Morganson et al. . |
| 4,520,221 | 5/1985 | Hsia Chen . |

OTHER PUBLICATIONS

Chemical Abstract, #145674a.
Fixed-Bed Catalytic Process to Produce Synthetic Lubricants from Decene-1, (Gulf Research and Development Co.), 1983, American Chemical Society.

Primary Examiner—Curtis R. Davis
Attorney, Agent, or Firm—Alexander J. McKillop; Charles J. Speciale; Robert B. Furr, Jr.

[57] ABSTRACT

An improved process for alkylation of isoparaffins with olefins to yield a product which includes a high proportion of highly branched paraffins for making gasoline having improved octane is taught. The improved process comprises isomerizing the olefins and then contacting effluent and isoparaffins with a composite catalyst comprising a Lewis acid and a large pore zeolite and/or a non-zeolitic inorganic oxide. The beneficial effects of low temperature operation and the use of water in the process are also noted. The process results in reduced catalyst aging and obviates environmental problems associated with prior art processes.

25 Claims, 3 Drawing Sheets

HETEROGENEOUS ISOPARAFFIN/OLEFIN ALKYLATION WITH ISOMERIZATION

This application contains related subject matter with applications Ser. No. 219,130, entitled Heterogeneous Isoparaffin/Olefin Alkylation Process; and application Ser. No. 219,129, entitled Heterogeneous Isoparaffin/Olefin Alkylation Process, all filed of even date, July 15, 1988.

FIELD OF THE INVENTION

The present invention relates to the art of improving octane rating of gasoline by alkylating an isoparaffin with an olefin stream which has previously been isomerized to provide an alkylate product useful as a high octane blending component in gasoline.

BACKGROUND OF THE INVENTION

This invention results from a need to improve octane ratings for gasoline. Isoparaffin-olefin alkylation is a means to produce highly branched paraffins which effects this octane improvement.

Alkylation is a reaction in which an alkyl group is added to an organic molecule. Thus, an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This is a very valuable blending component in the manufacture of gasolines because of its high octane rating.

Traditionally, the process in the industry includes the use of hydrofluoric acid or sulfuric acid and a catalysis carried out under controlled temperature conditions. Low temperatures are utilized in the sulfuric acid process to minimize the side reaction of olefin polymerization and the acid strength is generally maintained at 88 to 94% by the continuous addition of fresh acid and the continuous withdrawal of spend acid The hydrofluoric acid process is less temperature-sensitive and the acid is easily recovered and purified.

The typical types of alkylation currently used to produce high octane blending components, that is, the hydrofluoric acid and sulfuric acid alkylation processes, have inherent drawbacks including environmental concerns, acid consumption and sludge disposal. With the increasing demands for octane and the increasing environmental concerns, it has been desirable to develop an alkylation process based on a solid catalyst system. The catalyst of the present invention offers a refiner a less expensive, more environmentally acceptably and more selective alkylation process than the currently used hydrofluoric and sulfuric acid alkylation processes.

Although alkylation processes using liquid, acidic catalysts are commercially successful, inherent disadvantages arise, in addition to those mentioned above, in the use of such catalysts including handling and disposal of corrosive material.

Consequently, substantial efforts have been made to develop a viable isoparaffin-olefin alkylation process using a solid catalyst, rather than a liquid catalyst, which is commercially acceptable.

U.S. Pat. No. 3,862,258 teaches an alkylation process using a catalyst comprising a macroreticular acid cation exchange resin and boron trifluoride. According to the patent, the life of such a catalyst can be extended by the presence in the reaction mixture of closely controlled amounts of water which can be added to the feed as water or as water-forming compound.

U.S. Pat. No. 3,450,644 discloses a method for regenerating a zeolite catalyst used in hydrocarbon conversion processes involving carbonium ion intermediates.

U.S. Pat. No. 3,549,557 describes alkylation of isobutane with $C_2$-$C_3$ olefins using certain crystalline aluminosilicate zeolite catalysts in a fixed, moving or fluidized bed system.

U.S. Pat. No. 3,644,565 discloses alkylation of a paraffin with an olefin in the presence of a catalyst comprising a Group VIII noble metal present on a crystalline aluminosilicate zeolite. The catalyst is pretreated with hydrogen to promote selectivity.

U.S. Pat. No. 3,647,916 describes an isoparaffinolefin alkylation process featuring use of an ion-exchanged crystalline aluminosilicate, isoparaffin/olefin molar ratios below 3:1 and regeneration of the catalyst.

U.S. Pat. No. 3,655,813 discloses a process for alkylating $C_4$-$C_5$ isoparaffins with $C_3$-$C_9$ olefins using a crystalline aluminosilicate zeolite catalyst wherein a halide adjuvant is used in the alkylation reactor. The isoparaffin and olefin are introduced in to the alkylation reactor at specified concentrations and catalyst is continuously regenerated outside the alkylation reactor.

U.S. Pat. No. 3,706,814 discloses another zeolite-catalyzed isoparaffin-olefin alkylation process and further provides for the addition of $C_5+$ paraffins such as Udex raffinate or $C_5+$ olefins to the alkylation reactor feed and the use of specific reactant proportions, halide adjuvants, etc.

U.S. Pat. No. 3,236,671 discloses an alkylation reaction wherein crystalline aluminosilicate zeolites having silica to alumina mole ratios above 3 is used. The reference also discloses the use of various metals exchanged and/or impregnated on such zeolites.

U.S. Pat. No. 3,624,173 discloses an isoparaffinolefin alkylation, which uses crystalline aluminosilicate zeolites containing gadolinium.

U.S. Pat. No. 3,738,977 discloses alkylation of paraffins with ethylene using a zeolite catalyst which possesses a Group VII metal component. The catalyst is pretreated with hydrogen.

U.S. Pat. No. 3,917,738 describes a process for alkylating an isoparaffin with an olefin using a solid, particulate catalyst capable of absorbing the olefin. The isoparaffin and the olefin are admixed to form a reactant stream in contact with catalyst particles at the upstream end of an adsorption zone. Thereafter, the reactants are passed concurrently with the catalyst so that a controlled amount of olefin is adsorbed into the catalyst before the combination of reactants and catalyst is introduced into an alkylation zone. This controlled olefin adsorption is thought to prevent polymerization of the olefin during alkylation.

U.S. Pat. No. 4,384,161 describes a process of alkylating isoparaffins with olefins to provide alkylate using a large pore zeolite catalyst capable of absorbing 2,2,4trimethylpentane, for example ZSM-4, ZSM-20, ZSM-3, ZSM-18, zeolite Beta, faujasite, mordenite, zeolite Y and the rare earth metal-containing forms thereof, and a Lewis acid such as boron trifluoride, antimony pentafluoride or aluminum trichloride. The use of a large pore zeolite with a Lewis acid is reported to increase the activity and selectivity of the zeolite thereby affecting alkylation with high olefin space velocity and low isoparaffin/olefin ratio. According to the patent, problems arise in the use of solid catalysts in that they appear to age rapidly and cannot perform effectively at high olefin space velocity and the patent teaches the above solution to rectify the problem utilizing a zeolite type catalyst.

The article entitled *Fixed Bed Catalytic Process to Produce Synthetic Lubricants From Decene-1*, Ind. Eng. Chem. Prod. Res. Dev., Vol. 22, No. 4 (1983), teaches oligomerizing olefin to produce fluids with lubricating properties using a silica-$BF_3$-water catalyst. The authors further teach that with this system much of the BF3 can be recycled to minimize $BF_3$ consumption and disposal problems. The reference teaches that water is a necessary component of the system and that in its absence a $BF_3$-silica catalyst rapidly deactivates. The reference further teaches that for less reactive olefins, such as Decene-1, a useful degree of oligomerization is achieved only by adding a measurable quantity of an activator such as water or a primary alcohol to $B_3$. The authors further point out that other $BF_3$ activators, such as ethers, ketones, acids and anhydrides, have also been claimed to form good olefin oligomerization catalysts. The article states that the process disclosed there is to both minimize $BF_3$ consumption and disposal problems to produce a product having excellent lubricating properties through use of a catalyst requiring an activator like water.

In U.S. Pat. No. 4,308,414, an olefin, such as 1-decene, is oligomerized in the presence of a three-component catalyst comprising boron trichloride, a minute amount of water and a particulate absorbent material such as silica to a lubricating product predominating in those oligomer fractions having viscosities within the lubricating oil range such as the trimer and tetramer.

U.S. Pat. No. 4,429,177 further relates to a method for making lubricating oil utilizing a catalyst comprising boron trifluoride, a minute amount of elemental oxygen and a particulate absorbent material such as silica. The reference points out that the two component catalyst comprising a solid absorbent and boron trifluoride gradually loses activity after a period of continued use, which aging cannot be conveniently corrected by increasing the boron trifluoride pressure. As a solution, the reference teaches that this aging can be essentially prevented if a minute amount of elemental oxygen is fed to the reactor.

U.S. Pat. No. 3,997,621 relates to oligomerization of olefins catalyzed by boron trifluoride which is controlled to yield desired trimer as a dominant lubricant product by adding small amounts of ester together with water or alcohol promoter.

U.S. Pat. No. 4,365,105, also relates to oligomerizing an olefin in the presence of three-component catalyst used in making lubricating oils which comprises a particular silica absorbent with boron trifluoride and water absorbed on the silica.

U.S. Pat. No. 4,394,296 relates to a three-component catalyst used in making lubricating oils which comprises a particular silica absorbent with boron trifluoride and water absorbed on the silica.

U.S. Pat. No. 2,939,890 discloses a process for alkylating an aromatic hydrocarbon with an olefin-acing compound at alkylation conditions in the presence of an alkylation catalyst comprising boron trifluoride modified alumina. Subsequently, U.S. Pat. No. 3,131,230 discloses the importance of the presence of small amounts of water for maintaining catalyst activity. Both of these patents are limited to aromatic alkylation processes.

U.S. Pat. No. 2,804,491 relates to a isoparaffin/olefin alkylation to make gasoline at temperatures between $-20°$ and $150°$ F. utilizing a two component catalyst comprising essentially excess $BF_3$ with a "silica stabilized gel alumina". No activators are taught.

In the past, severe activity and stability problems have been noted with respect to zeolite based systems. U.S. Pat. Nos. 3,251,902 and 3,893,942, as well as French Pat. No. 1,593,716 and the article to Kirsh and Potts, Div. of Pet. Chem. A.C.S., 15, A109 (1970) exemplify these problems. Improved stability was noted when a Lewis acid such as $BF_3$ was used in combination with macroreticular acid cation exchange resins as pointed out in U.S. Pat. No. 3,855,342. More recently, the use of $BF_3$ in combination with large pore zeolites such as ZSM-4 and Beta has been reported to effectively catalyze isoparaffin/olefin alkylation reactions. See U.S. Pat. No. 4,384,161. However, only applicants have achieved advantages compared to these previous teachings by the use of a combined isomerization/alkylation process where the alkylation catalyst comprises a Lewis acid, such as $BF_3$, in combination with a large pore zeolite, such as zeolite Beta and/or non-zeolitic solid inorganic oxide, such as $SiO_2$ or $Al_2O_3$, in the presence of closely controlled amounts of water to produce higher octane gasoline and to reduce catalyst aging.

U.S. Pat. 3,467,728 relates to a process for isomerizing olefinic hydrocarbon, such as 1-butene or 1-pentene by contacting the hydrocarbon with a catalyst comprising a crystalline alumina silicate combined with a substantially anhydrous boron halide.

U.S. Pat. No. 3,800,003 relates to a process for producing an alkylation reaction product from an isoparaffinic reactant and an olefinic reactant containing 1-butene, 2-butene and isobutene which includes passing the olefinic reactant through an isomerization zone. The isomerization catalyst comprises a crystalline aluminosilicate combined with a substantially anhydrous boron halide which can be boron trifluoride. Conventional catalysts are utilized for the alkylation reaction and include sulfuric acid and hydrogen fluoride catalyst which have the disadvantages set forth above.

Chemical abstract No. 145674a refers to an article discussing the effect of moisture and boron fluoride on the catalytic activity of aluminum oxide-boron fluoride. The abstract reports that the degree of catalyst poisoning due to moisture decreases with increasing temperature of catalyst preparation and with $BF_3$ content in the catalyst. It further reports that the addition of $BF_3$ into the inlet hydrocarbons prevents the poisoning and regenerates the activity of poisoned catalyst by forming $BF_3 \cdot H_2O$ and $BF_3 \cdot H_2O$ aducts. The abstract further reports that the effect of moisture in inlet hydrocarbons or in the air during the catalyst preparation and of free $BF_3$ added into a reactor on the catalytic activity of $Al_2O_3$–$BF_3$ alkylation catalyst was investigated on the alkylation of $C_4H_{10}$ with propylene.

Thus, this invention overcomes the problems posed by the prior art in that catalyst aging is significantly reduced. Furthermore, this process effects improved octane ratings for gasolines by utilizing a combined isomerization/alkylation process utilizing heterogeneous alkylation catalyst which includes the use of water to active said catalyst.

The preceding references are hereby incorporated by reference.

SUMMARY OF THE INVENTION

This invention relates to an alkylation process for producing high octane gasoline comprising isomerizing the olefin feed to substantially reduce its alpha olefin content, effecting reaction of an isoparaffin containing from 4 to 20 carbon atoms with the isomerized olefin feed containing from 2 to 12 carbon atoms at from about −40° C. to about 500° C. and at a pressure in the range of subatmospheric to about 5000 psig using a hydrocarbon feed wherein the molar ratio of the isoparaffin to the olefin in the combined hydrocarbon feed is from about 1:1 to about 50:1 in contact with a composite catalyst comprising a Lewis acid with a large pore zeolite and/or a non-zeolitic solid inorganic oxide in the presence of a controlled amount of water.

DESCRIPTION OF THE INVENTION

Figure 1:
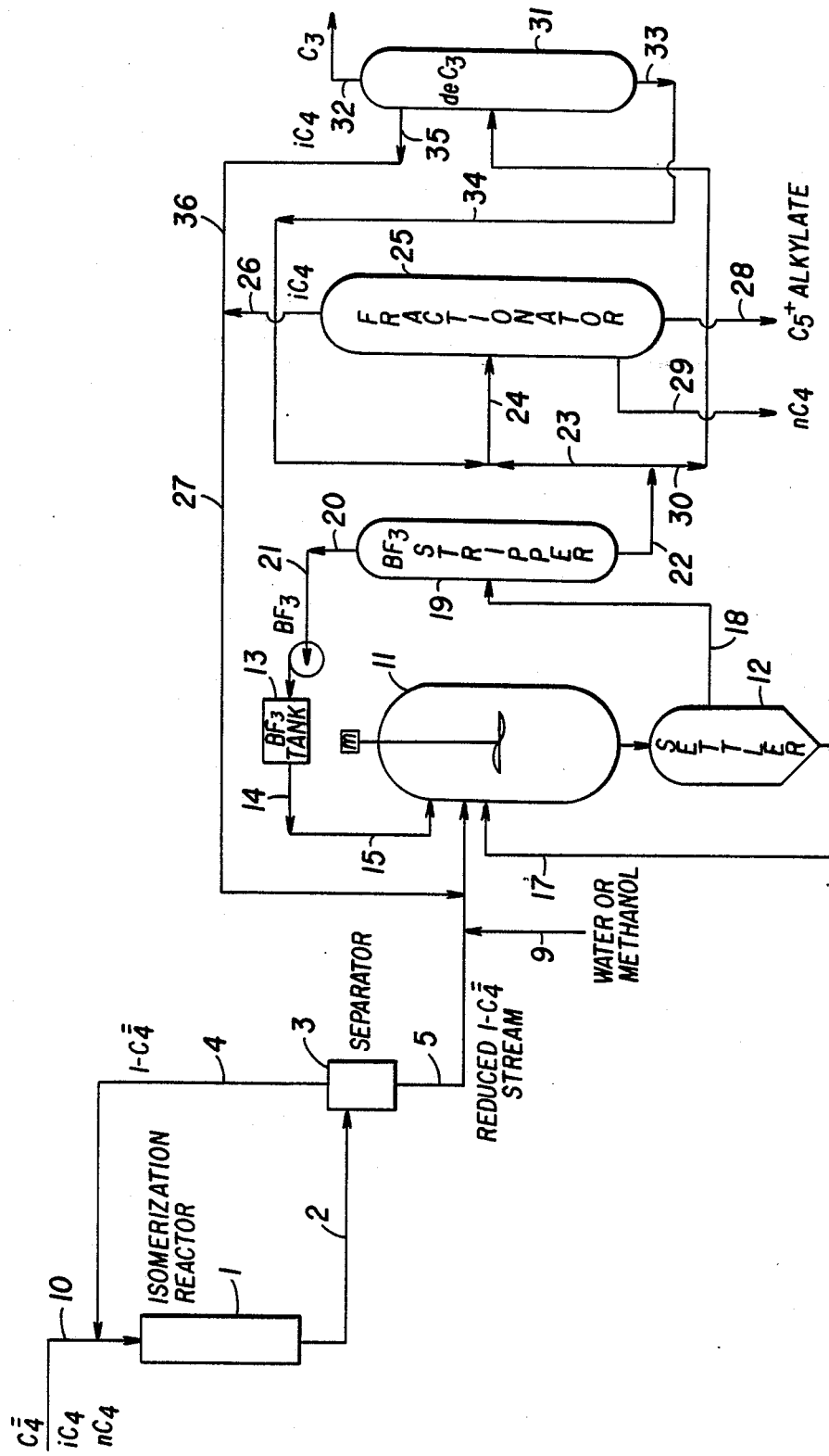
FIG. 1 shows a simplified schematic flow diagram of the continuous alkylation unit used in the present invention. This is presented without intending to limit the scope of this invention.

The alkylation of isobutane with light olefins plays an important role in the manufacture of high octane gasoline blending stocks with alkylate typically comprising 10 to 15% of the gasoline pool. Alkylate is a particularly valuable portion of the gasoline pool. Alkylate is a particularly valuable portion of the gasoline pool as it has both high research and motor octane, contains no olefins or aromatics and little or no sulfur, demonstrates excellent stability and is clean burning.

Applicants have developed a process for producing high octane gasoline using a combined isomerization/alkylation process. It includes a novel isoparaffin/olefin alkylation catalyst. The catalyst system includes a Lewis acid, such as $BF_3$, in combination with a large pore zeolite, such as zeolite Beta, and/or a non-zeolitic solid inorganic oxide, such as $SiO_2$ or $Al_2O_3$, to promote paraffin/olefin alkylation, all in the presence of a closely controlled amount of water. The Lewis acid is to be maintained at a level in excess of that required to saturate the solid catalyst. The resulting alkylate is of a high quality based on both research and motor octane and is particularly suited for blending into the gasoline pool. Furthermore, the process exhibits increased octanes over prior art processes by operating at reduced temperature.

The olefinic feed in the present process is first contacted with an isomerization catalyst in an isomerization zone at olefin isomerization conditions. Isomerization catalysts which can be used in the isomerization operation of the present invention include catalysts which produce a shift of the double bond in 1-butene to a more central position in the hydrocarbon molecule to form 2-butene. Various conventional catalysts are suitable, including, for example, alumina, silica, zirconia, chromium oxide, boron oxide, thoria, magnesia, aluminum sulfate, and combinations of two or more of the foregoing. Also suitable for use in the isomerization operation as an isomerization catalyst is a boron halide-modified metal oxide such as boron halide-modified substantially anhydrous or hydrous alumina. Thermal isomerization may be utilized, but suffers from the defect of producing excessive amounts of side products.

The isomerization step may also include a separation section to remove unconverted 1-butene. This may also include recycling 1-butene to the isomerization reactor. Alkylation follows isomerization.

Zeolites used in the present invention include those which have pores sufficiently large to physically absorb 2,2,4-trimethylpentane such as, for example, ZSM-3, ZSM-4, ZSM-12, ZSM18. ZSM-20, zeolite Beta, zeolite L, mordenite, faujasite, zeolite Y, and the rare earth metal containing forms of the above. A wide range of silica-to-alumina ratios, e.g., from at least about 10:1 to about 200:1 and even higher, e.g., approaching infinity, can be used. For the purposes of this invention, zeolite Y includes zeolite Y in its as synthesized form, as well as its variant forms including framework dealuminated zeolite Y, e.g., ultrastable Y (USY) described in U.S. Pat. No. 3,293,192 and LZ-210 described in U.S. Pat. No. 4,503,023.

The large pore zeolite selected for use in the improved alkylation process of this invention can possess an alpha value over a wide range of from less than 1 to over 1000. "Alpha value", or "alpha number", is a measure of zeolite acidic functionality and is more fully described together with details of its measurement in U.S. Pat. No. 4,016,218, *J. Catalysis*, 6, PP. 278–287 (1966) and *J. Catalysis*, 61, pp. 390–396 (1980). Zeolites of low acidity (alpha values of less than about 200) can be achieved by a variety of techniques including (a synthesizing a zeolite with a high silica/alumina ratio, (b) steaming, (c) steaming followed by dealuminization and (d) substituting framework aluminum with other species. For example, in the case of steaming, the zeolite can be exposed to steam at elevated temperatures ranging from about 500° to about 1200° F. and preferably from about 750° to about 1000° F. This treatment can be accomplished in an atmosphere of 100% steam or an atmosphere consisting of steam and a gas which is substantially inert to the zeolite. A similar treatment can be accomplished at lower temperatures using elevated pressure, e.g., at from about 350° to about 700° F. with from about 10 to about 200 atmospheres. Specific details of several steaming procedure may be gained from the disclosures of U.S. Pat. Nos. 4,325,994; 4,374,296 and 4,418,235, the contents of which are incorporated by reference herein. Aside from, or in addition to, any of the foregoing procedures, the surface acidity of the zeolite can be eliminated or reduced by treatment with bulky reagents as described in U.S. Pat. No. 4,520,221, the contents of which are incorporated by reference herein.

In practicing the improved alkylation process of the present invention, it may be advantageous to incorporate the above-described large pore zeolites into some other material, i.e., a matrix or binder, which is stable under the conditions used in the process. Useful matrix materials include both synthetic and naturally-occurring substances, e.g., inorganic materials such as clay, silica and/or metal oxides. Such materials can be either naturally-occurring or can be obtained as gelatinous precipitates or gels including mixtures of silica and metal oxides. Naturally-occurring clays which can be composited with the zeolite include those of the montmorillonite and kaolin families, which families include the sub-bentonites and the kaolins commonly known as Dixie, McNamee-Georgia and Florida clays or others in which the main mineral constituent is haloysite, kaolinite, dickite, nacrite or anauxite. Such clays can be used in the raw state as originally mined or initially subjected to calcination, acid treatment or chemical modification.

In addition to the foregoing materials, the zeolites used herein can be composited with a porous matrix material such as carbon, alumina, titania, zirconia, silica, silica-alumina, silica-magnesia, silica-zirconia, silica-thoria, silica-beryllia, silica-titania, etc., as well as ternary oxide compositions, such as silica-alumina-thoria, silica-alumina-zirconia, silica-alumina-magnesia, silica-magnesia-zirconia, etc. The matrix can be in the form of a cogel. The relative proportions of zeolite component and matrix material, on an anhydrous basis, can vary widely with the zeolite content ranging from between 1 to about 99 wt %, and more usually in the range of about 5 to about 90 wt % of the dry composite.

In some cases, it may be advantageous to provide the zeolite component of the alkylation catalyst herein as an extrudate bound with a low acidity refractory oxide binder using the method described in commonly assigned, copending U.S. patent application Ser. No. 44,639, filed May 1, 1987, the contents of which are incorporated by reference herein. In accordance with this method, a homogeneous mixture of a large pore zeolite, such as zeolite Beta, water and a low acidity refractory oxide binder, e.g., silica, which contains at least an extrusion-facilitating amount of the binder provided in a colloidal state and which is substantially free of added alkali metal base and/or basic salt, is formed into an extrudable mass. The mass is extruded, and the resulting extrudate is dried and calcined.

The original cations associated with the zeolite utilized herein can be replaced by a wide variety of other cations according to techniques well known in the art, e.g., by ion-exchange. Typical replacing cations including hydrogen, ammonium, alkyl ammonium and metal cations, and their mixtures. In the case of metal cations, particular preference is given to such metals as magnesium, zinc, calcium, zinc, and mixtures thereof. A typical ion-exchange technique involves contacting the particular zeolite with a salt of the desired replacing cation. Although a wide variety of salts can be used, particular preference is given to chlorides, nitrates and sulfates.

Representative ion-exchange techniques are disclosed in a number of patents including U.S. Pat. Nos. 3,140,249; 3,140,251; 3,140,253 and 3,702,886.

Following contact with a solution of the desired replacing cation, the zeolite is then preferably washed with water and dried at a temperature ranging from 150° to about 600° F. Thereafter it is calcined in air or other inert gas at temperatures ranging from about 500° to 1500° F. for periods of time ranging from 1 to 48 hours or more.

It is also possible to treat the zeolite with steam at elevated temperatures ranging from 800° F. to 1600° F. and preferably 1000° F. to 1500° F., if such is desired. The treatment may be accomplished in atmospheres consisting partially or entirely of steam.

A similar treatment can be accomplished at lower temperatures and elevates pressures, e.g., 350°-700° F. at 2 to about 200 atmospheres.

As previously stated, the alkylation catalysts, described herein comprise a large pore zeolite of the aforedescribed type and/or a non-zeolitic solid inorganic oxide in combination with a Lewis acid. A Lewis acid is generally considered to be a molecule which is capable of combining with another molecule or ion by forming a covalent chemical bond with two electrons from the second molecule or ion, that is, the Lewis acid is an electron acceptor. Examples of Lewis acids include boron trifluoride ($BF_3$), boron trichloride ($BCl_3$), antimony pentafluoride ($SbF_5$), and aluminum chloride ($AlCl_3$). The present invention comtemplates the use of all Lewis acids such as those set forth in *Friedel-Crafts and Related Reactions,* Interscience Publishers, chapters III and IV (1963), which is incorporated by reference. Boron trifluoride is preferred for use in the alkylation process of this invention.

Consider the catalyst comprising the Lewis acid and inorganic oxide. The inorganic oxide of this catalyst may be selected from among the diverse inorganic oxides including alumina, silica, boria, oxides or phosporus, titanium dioxide, zirconium dioxide, chromia, zinc oxide, magnesia, calcium oxide, silica-alumina, silica-magnesia, silica-alumina-magnesia, silica-alumina-zirconia, chromia-alumina, alumina-boria, silica-zirconia, etc. and the various naturally occurring inorganic oxides of various states of purity such as bauxite, clay, diatomaeous earth, etc. The preferred inorganic oxides are amorphous silicon dioxide and aluminum oxide.

It is also recognized that the aforementioned solid inorganic oxides may be used as binder material in a large pore zeolite containing catalyst. This combination of zeolite and solid inorganic oxide is contemplated and is within the scope of the present invention.

The operating temperature of the alkylation process can extent over a fairly broad range, for example, from about −40° to about 500° C. and is preferably within the range of from about −40° C. to about 100° C. The practical upper operating temperature will often be dictated by the need to avoid an undue occurrence of undesirable side reactions. Lower temperatures are preferred to maximum alkylate octane.

The pressures used in the present process can extend over a considerably wide range, for example, from subatmospheric to about 5000 psig, preferably to about 500 psig.

The amount of catalyst used in the present process can be varied over relatively wide limits. In general, the amount of catalyst as measured by the weight hourly space velocity of the olefin can range from about 0.01 to about 100. The amount of catalyst selected for a particular reaction will be determined by several variables including the reactants involved as well as the nature of the catalyst and the operating conditions used.

The particular operating conditions used in the present process will depend on the specific alkylation reaction being effected. Such conditions as temperature, pressure, space velocity and molar ratio of the reactants will have important effects on the overall process. Also, the operating conditions for the alkylation reaction according to this process may be varied so that the same may be conducted in gaseous phase, liquid phase or mixed liquid-vapor phase, depending upon product distribution, degree of alkylation, as well as the pressures and temperatures at which the alkylation is effected.

The isoparaffin reactant used in the present alkylation process is one possessing up to about 20 carbon atoms and preferably one having from about 4 to about 8 carbon atoms as, for example, isobutane, 3-methylhexane, 2-methylbutane, 2,3-dimethylbutane, 2,3-dimethylpentane and 2,4-dimethylhexane.

The olefin reactant used generally contains from 2 to about 12 carbon atoms. Representative examples are ethylene, propylene, 1-butene, 2-butene, isobutylene, pentenes, etc. Particularly preferred are $C_3$ and $C_4$ olefins and mixtures thereof.

In general, the relative molar ratio between the isoparaffin reactant and the olefin alkylating agent can be from about 1:1 to about 50:1 and is preferably in the range of from about 5:1 to about 25:1.

A critical requirement of the improved alkylation process herein is that water be added to the alkylation reactor, that is, at a rate on average of from about 0.1 ppmw to about 1 wt %, based upon total hydrocarbon feed rate, preferably at a rate from about 0.1 to about 500 ppmw. The water can be supplied as such or be a feed material which provides water under the alkylation condition selected. Suitable water-forming materials which can be introduced into the reactor without interfering with the desired alkylation include monohydric and dihydric alcohols which yield water upon undergoing dehydration. Of this group, particular preference is accorded the aliphatic alcohols, especially those containing 1 to 6 carbon atoms, for example, methanol, ethanol, isopropanol, t-butyl alcohol and isopentyl alcohol. The water and/or water-producing material can be added directly to the reactor, that is, as part of the feed and/or it can be incorporated in the catalyst, either by direct contact or by exposing the catalyst to an atmosphere of water and/or water-forming material. The amount of preintroduced water into the catalyst ranges from about 0.5 to about 25 percent by weight of the catalyst, preferably from about 1 to about 10 percent.

A suitable system for carrying out the improved alkylation process of this invention on a continuous bases is shown in FIG. 1. Note that while this example deals specifically with a feed comprising a mixture of butene isomers, this is not intended to limit the scope of the invention. As depicted, feed is introduced via line 10 into isomerization reactor 1. Effluent is removed and sent via line 2 to separator 3. There 1-butene is separated and recycled to reactor 1 and while the resultant reduced 1-butene stream is sent via line 5 to reactor 11. Water and/or a water-producing material such as methanol is introduced through line 9 to a stream containing effluent from the isomerization reactor 1, combined with recycle isobutane and fed to stirred reactor 11 containing the zeolite or inorganic oxide. $BF_3$ is introduced from tank 13 through lines 14 and 15 into the reactor. The amount of $BF_3$ introduced is such as to exceed that necessary to saturate the zeolite or inorganic oxide. Catalyst slurry is removed from the reactor and is introduced to settling vessel 12. The recovered zeolite or inorganic oxide is recycled to the alkylation reactor by line 17. The hydrocarbon product mixture is removed from the settling vessel through line 18. It is introduced into $BF_3$ stripper 19 from which $BF_3$ is removed as overhead through line 20 and recycled through line 21 to $BF_3$ holding tank 13. The remaining hydrocarbon product mixture is withdrawn from the $BF_3$ stripper through line 22. A portion of such hydrocarbon product mixture is introduced via lines 23 and 24 to fractionator 25. Unreacted isobutane is removed as overhead through line 26 and recycled through line 27 to the reactant feed stream, line 5. Desired $C_5^+$ alkylate product is withdrawn from the bottom of a fractionator 25 through line 28. Any normal butane may be withdrawn from the fractionator through line 29. The remaining portion of the hydrocarbon product mixture passing through line 22 from $BF_3$ stripper 19 is conducted through line 30 to depropanizer 31 from which propane is removed as overhead through line 32. Desired heavy fraction ($C_4^+$) is removed as bottoms through line 33 and recycled via lines 34 and 24 to fractionator 25. Isobutane is removed from depropanizer 31 through line 35 and recycled through lines 36 and 27 to the initial reaction feed line 5.

EXPERIMENTATION

The following experimentation will serve to illustrate the process of the invention without limiting it.

Unless otherwise noted in the Example, the results were obtained in a 300 ml stirred autoclave reactor at the operating conditions set forth in Table 1.

TABLE 1

| $BF_3$ PROMOTED ALKYLATION OPERATING CONDITIONS | |
|---|---|
| Temperature, °C. | 0–20 |
| Pressure, psig | 150 |
| Stirring Rate, rpm | 1900 |
| $BF_3$ Feed Rate, wt % of hydrocarbon feed | 3.0 |
| Hydrocarbon Feed, i-$C_4$/olefin ratio | 10/1 |
| Olefin WHSV, $hr^{-1}$ | 1.2 |

Examples 1 and 2 demonstrate the beneficial effects of $H_2O$ addition on the $BF_3$/zeolite Beta and $BF_3/SiO_2$ catalyst systems, respectively. In the former case, the water was preintroduced into the catalyst; while in the latter case, the water was cofed with the hydrocarbon reactants. Example 3 shows the beneficial effect of reduced temperature operation for the $BF_3/SiO_2$ catalyst. Example 4 illustrates the importance of olefin isomerization prior to alkylation for the process of the current invention.

In a standard start-up procedure, 10 grams of catalyst is placed in the 300 ml autoclave reactor, and about 300 ml of isobutane is charged to fill the reactor. The resulting mixture is cooled to the desired temperature with constant stirring at 1900 rpm and $BF_3$ gas is introduced into the reactor. After $BF_3$ breakthrough is observed, the $BF_3$ flow rate is then reduced to a level equivalent to 3 wt % of total hydrocarbon feed rate. At this point, the isobutane/olefin mixture is continuously fed into the reactor to initiate the catalytic alkylation. The operating conditions as set forth in Table 1 are 150 psig, 0°–20° C., 1900 RPM, 1.2 WHSV based on olefin and 3.0 wt % $BF_3$ based on total hydrocarbon feed. The product is continuously withdrawn from the reactor and is weathered to atmospheric pressure via a back pressure regulator and then sent to a receiver which is kept at 0° C. Periodically, the product is drained from the receiver and weathered at room temperature prior to analysis.

An on-line gas chromatograph coupled with an automatic sampling device is used to monitor the course of the alkylation reaction. The isobutane (C.P. grade), isobutane/olefin mixtures and $BF_3$ (C.P. grade) are all used without further purification.

EXAMPLE 1

Two zeolite Beta catalysts containing 6 and 16 weight percent water, respectively, are used in the alkylation of isobutane with butene-1. The varying water contents are obtained by exposing separate portions of the zeolite catalyst to low and high moisture content atmospheres.

Tables 2 and 3 show the yield/octane results for the low and high water-containing zeolite Beta catalysts, respectively. In both cases, the $C_5^+$ yield data indicate that alkylation is essentially complete. As the data show, a significant improvement in the alkylate quality is observed for the 16 weight percent water-content zeolite Beta catalyst. Specifically, the octane numbers from the high water-content catalyst are substantially higher over the course of the experiment. In addition, the $C_9^+$ content of the alkylate product is reduced with the high moisture content catalyst.

TABLE 2

PERFORMANCE OF "LOW WATER CONTENT" ZEOLITE BETA (6 WT % $H_2O$) ISOBUTANE/BUTENE-1 ALKYLATION

| Time on Stream, hr. | 4 | 10 | 20 |
|---|---|---|---|
| Yield, g $C_5^+$/g Olefin Converted | 2.1 | 2.3 | 2.2 |
| Yields in $C_5^+$, wt % | | | |
| $C_5-C_7$ | 0.6 | 1.0 | 1.7 |
| $C_8$ | 88.2 | 89.9 | 86.4 |
| $C_9^+$ | 11.2 | 9.1 | 11.9 |
| Octane | | | |
| RON + O | 71.0 | 71.8 | 67.3 |
| MON + O | 76.1 | 77.6 | 70.3 |

TABLE 3

PERFORMANCE OF "HIGH WATER CONTENT" ZEOLITE BETA (16 WT % $H_2O$) FOR ISOBUTANE/BUTENE-1 ALKYLATION

| Time on Stream, hr. | 4 | 8 | 18 |
|---|---|---|---|
| Yield, g $C_5^+$/g Olefin Converted | 2.2 | 2.3 | 1.9 |
| Yields in $C_5^+$, wt % | | | |
| $C_5-C_7$ | 1.8 | 0.7 | 1.5 |
| $C_8$ | 90.3 | 95.9 | 94.4 |
| $C_9^+$ | 7.9 | 3.4 | 4.1 |
| Octane | | | |
| RON + O | 77.1 | 79.3 | 86.0 |
| MON + O | 80.1 | 80.9 | 81.4 |

EXAMPLE 2

The purpose of this example is to demonstrate the effect of intermittent $H_2O$ addition to the hydrocarbon feed on the resulting alkylate quality. The catalyst used in this example is a commercially available amorphous $SiO_2$ (0.5 wt % $Al_2O_3$) which is calcined at 1000° F. and sized to 100/200 mesh. The hydrocarbon feed is a simulated commercial feed (approximately 10/1 i-$C_4$/mixed olefins) approximating the $C_3^=/C_4^=$ fraction produced from an FCC as specified in Table 4.

TABLE 4

| MIXED $C_3/C_4$ OLEFIN DISTRIBUTION, WT % | |
|---|---|
| Propylene | 42.5 |
| 1-Butene | 13.7 |
| Cis and Trans-2-Butene | 28.2 |
| Isobutylene | 15.6 |

The other operating conditions are as set forth in Table 1 with a temperature of 20° C. A comparison of the yield and octane results for the $BF_3/SiO_2$ catalyst system both with and without added water is shown in Table 5. These two alkylation runs are designated as Examples 2B and 2A, respectively. In the case of $H_2O$ addition, water is added intermittently throughout the run at an average rate of about 100 ppm based upon total hydrocarbon feed rate.

TABLE 5

THE EFFECT OF $H_2O$ ADDITION ON $BF_3$-PROMOTED ALKYLATION

| EXAMPLE | 2A | 2B |
|---|---|---|
| Catalyst System | $BF_3/SiO_2$ | $BF_3/SiO_2/H_2O$ |
| Yield, g $C_5^+$/g Olefin Converted | 2.1 | 2.1 |
| Hydrogen Transfer, Vol % | 1.5 | 1.7 |
| Yields in $C_5^+$, Wt % | | |
| $C_5$ | 3.4 | 2.7 |
| $C_6$ | 3.3 | 2.3 |
| $C_7$ | 29.1 | 27.1 |
| $C_8$ | 54.7 | 61.4 |
| $C_9^+$ | 9.6 | 6.4 |
| RON + O | 91 | 93 |
| MON + O | 89 | 90 |

The results show that alkylation is essentially complete in both cased based upon the high $C_5^+$ yield/g of olefin converted. However, low level $H_2O$ addition substantially improves alkylate quality over $B_3$/silica catalyst alone as seen by the increased research and motor octanes and reduced $C_9^+$ yield.

EXAMPLE 3

Example 2A is repeated with the exceptions noted in Table 6. This example shows a comparison between the $BF_3/SiO_2$ catalyst of the present invention and a commercially available HF catalyst. The experiment also shows the effect of reduced temperature on the catalyst of the present invention.

TABLE 6

$BF_3$-PROMOTED ALKYLATION COMPARISON WITH COMMERCIAL HF MIXED $C_3/C_4$ OLEFIN FEED

| CATALYST | $BF_3/SiO_2$ | | HF |
|---|---|---|---|
| Temperature, °F. | 32 | 70 | 70 |
| External i-$C_4$/Olefin | 10/1 | 10/1 | 14/1 |
| Yield, g $C_5^+$/g Olefin Converted | 2.2 | 2.1 | 2.1 |
| Hydrogen Transfer, Vol % | 0.6 | 1.5 | 14 |
| Yields in $C_5^+$, Wt % | | | |
| $C_5$ | 2.1 | 3.4 | 3.7 |
| $C_6$ | 2.5 | 3.3 | 2.2 |
| $C_7$ | 36.3 | 29.1 | 24.3 |
| $C_8$ | 53.7 | 54.7 | 61.1 |
| $C_9^+$ | 5.5 | 9.6 | 8.7 |
| RON + O | 94 | 91 | 92.6 |
| MON + O | 92 | 89 | 91.6 |

These results show that low temperature operation with the catalyst of the present invention can improve octane over a prior art process at ambient temperature. Reducing temperature below about 70° F. with HF alkylation will not effect octane appreciably.

EXAMPLE 4

The concept developed here revolves around the extreme sensitivity of the Lewis acid systems to the 1-$C_4^=$ isomer as demonstrated in Table 7 where $BF_3$ is the Lewis acid and zeolite Beta is the promoted solid. The octane number of the product (72 R+O) is substantially less than that from both HF and $H_2SO_4$ alkylation (94 and 97 R+O, respectively). Results with 2-$C_4^=$ and i-$C_4^=$ are much more similar in their product octanes as shown in Table 8. In the case of isobutane/1-butene alkylation, the low octanes with $BF_3$/zeolite result from the high concentration of dimethylhexanes vs the preferred trimethylpentanes. These results are attributed to low rates of olefin isomerization in Lewis acid/solid catalyst systems before alkylation and/or a low rate of skeletal isomerization of the C<sub>8</sub> product after alkylation. In the following tables 1-butene, 2-butene and isobutene are abbreviated 1-$C_4^=$, 2-$C_4^=$ and i-$C_4^=$, respectively.

TABLE 7
ALKYLATION WITH 1-BUTENE FEED

|  | Zeolite/BF$_3$ | HF | H$_2$SO$_4$ |
|---|---|---|---|
| Temperature (Degree F.) | 32 | 70 | 52 |
| External i-C$_4$/Olefin | 10 | 12 | 10 |
| Yields (g C$_5^+$/g olefin) | 2.0 | 2.0 | 2.0 |
| Product Distribution |  |  |  |
| DMH | 83.0 | 22.1 | 10.0 |
| TMP | 4.1 | 68.2 | 72.0 |
| C$_9^+$ | 11.4 | 5.7 | 8.0 |
| RON + O | 72 | 94 | 97 |
| MON + O | 77 | 92 | — |

TABLE 8
2-BUTENE AND ISOBUTYLENE ALKYLATION COMPARISONS
Same temperatures and External i-C$_4$/Olefin Ratios as in Table 7

|  | Zeolite/BF$_3$ | | HF | | H$_2$SO$_4$ | |
|---|---|---|---|---|---|---|
| ISOMER | 2-C$_4^=$ | i-C$_4^=$ | 2-C$_4^=$ | i-C$_4^=$ | 2-C$_4^=$ | i-C$_4^=$ |
| RON + O | 99.7 | 99.6 | 99 | 98 | 96 | 92 |
| MON + O | 96.4 | 96.0 | 96 | 96 | — | — |
| YIELD IN C$_5^+$ |  |  |  |  |  |  |
| Dimethylhexanes | 9.5 | 8.3 | 6.9 | 3.4 | 10 | 15 |
| Trimethylpentanes | 70.5 | 71.2 | 85.6 | 86.1 | 72 | 51 |
| C$_9^+$ | 9.3 | 10.8 | 4.1 | 5.3 | 8 | 11 |

This lack of skeletal isomerization is unexpected and detrimental with 1-butene in the feed but can be taken advantage of when the feed is comprised primarily of 2-butene and isobutylene.

Figure 2:
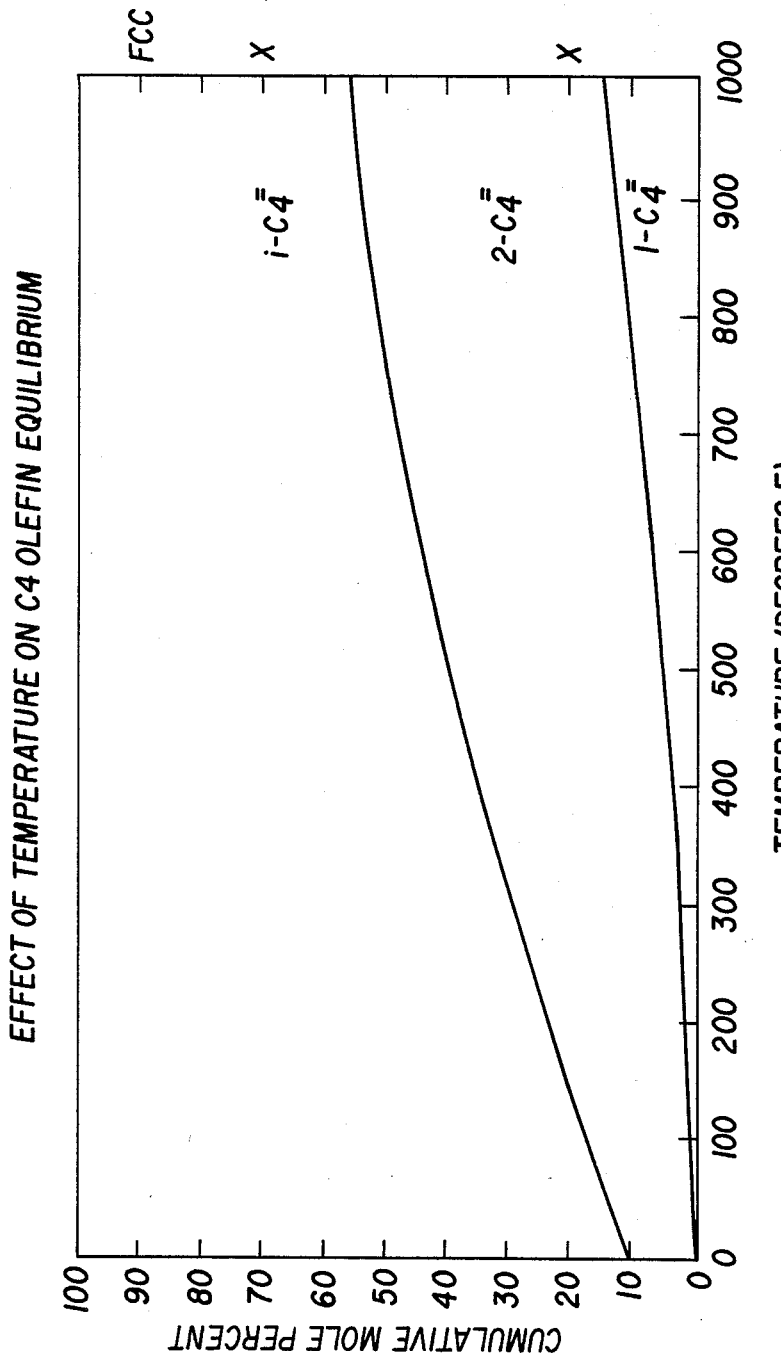
FIG. 2 shows the effect of temperature on $C_4$ olefin equilibrium.

A typical breakdown of the C$_4$ olefin fraction from an FCC unit is shown in FIG. 2 and is approximately 20/50/30 1-$C_4^=$/2-$C_4^=$/i-$C_4^=$. Using linear blending based on data contained in Tables 7 and 8 without feed isomerization, this would produce gasolines with the following octane qualities:

| RON + O | |
|---|---|
| BF$_3$/zeolite | 94.1 |
| HF | 97.7 |
| H$_2$SO$_4$ | 95.0 |

Figure 3:
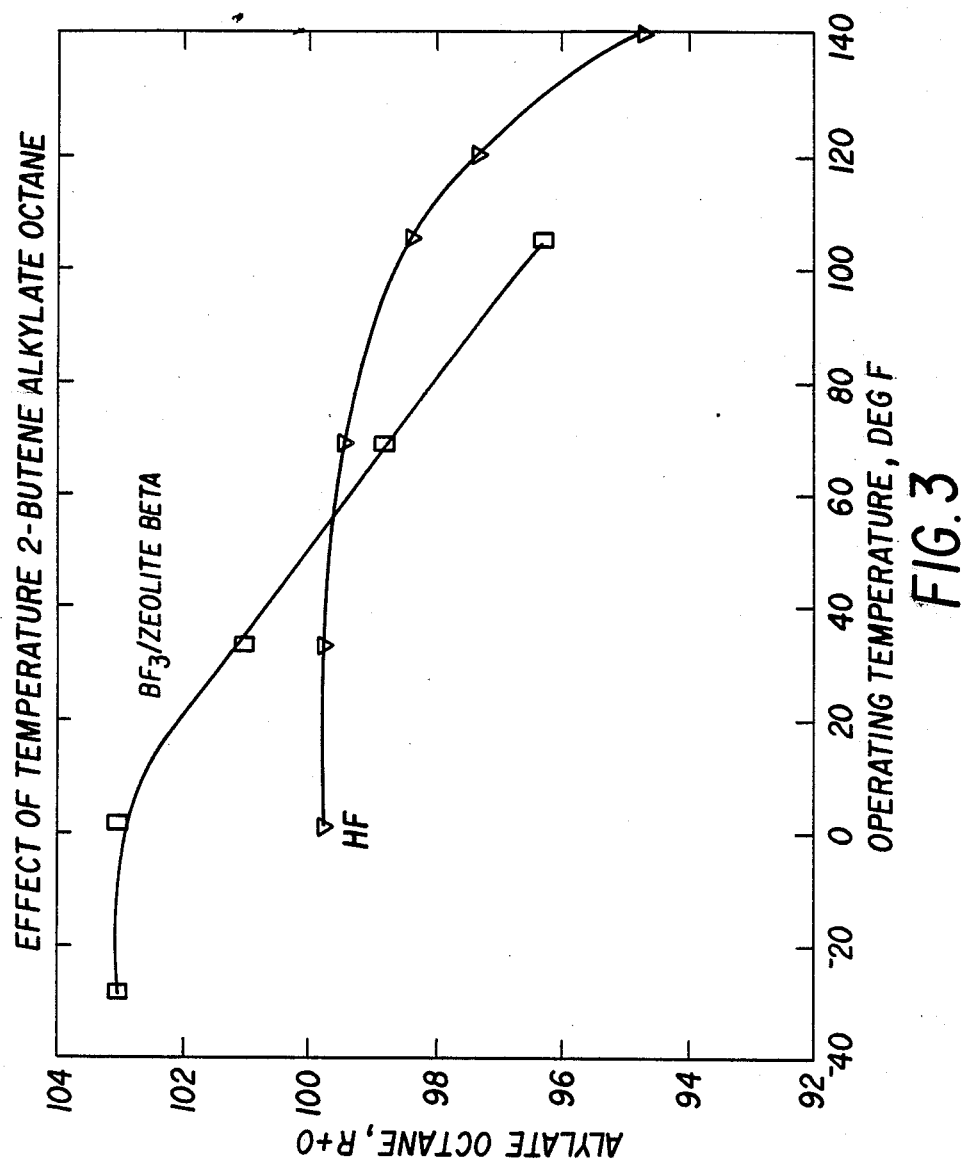
FIG. 3 shows the effect of temperature on octane for the alkylation of isobutane with 2-butene.

FIG. 3 shows the effect of temperature on alkylate octane for 2-butene. The octane rating for BF$_3$/zeolite Beta can be substantially improved over HF by coupling this low temperature advantage with olefin isomerization before alkylation utilizing a scheme such as shown in FIG. 1. With the combined effects of feed isomerization and low temperature operation, resulting octanes are:

| RON + O | |
|---|---|
| BF$_3$/zeolite | 101–103 |
| HF | 100 |
| H$_2$SO$_4$ | 98–100 |

Thus, under proper conditions, the proposed combined isomerization/alkylation process has the ability to produce +1-3 RON+O over conventional alkylation technology. Furthermore, additional octane benefits arise from the controlled addition of water to the Lewis acid/solid catalyst system as illustrated in Examples 1 and 2.

Thus, applicants have found the combination of isomerization/alkylation when alkylation is of the Lewis acid/solid catalyst type in the presence of added water to have the following advantages:

The advantages of isomerization prior to alkylation when the olefin feed contains 1-butene are substantially greater with the Lewis acid system than with the HF system.

The combination of isomerization/alkylation and low temperature with the Lewis acid system in the presence of added water can be used to produce an alkylate of substantially higher octane than either HF or sulfuric acid (H$_2$SO$_4$) alkylation.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. A continuous alkylation process for producing high octane gasoline comprising isomerizing the olefin feed to substantially reduce its alpha olefin content, effecting reaction of an isoparaffin containing from 4 to 20 carbon atoms with the isomerized olefin feed containing from 2 to 12 carbon atoms at from about −40° C. to about 500° C. and at a pressure in the range of subatmospheric to about 5000 psig using a hydrocarbon feed wherein a molar ratio of the isoparaffin to the olefin in the combined hydrocarbon feed is from about 1:1 to about 50:1 in contact with a composite catalyst comprising a Lewis acid with large pore zeolite and/or a nonzeolitic solid inorganic oxide in the presence of a controlled amount of water.

2. The process of claim 1, wherein the isoparaffin contains from 4 to 6 carbon atoms and the olefin contains from 2 to 6 carbon atoms.

3. The process of claim 1, wherein the Lewis acid is BF$_3$, BCl$_3$, SbF$_5$ and/or AlCl$_3$.

4. The process of claim 1, wherein the inorganic oxide is SiO$_2$ or Al$_2$O$_3$.

5. The process of claim 1, wherein the reaction is conducted under sufficient pressure to maintain at least one of the reactants in the liquid phase.

6. The process of claim 1, wherein the reaction is carried out within a temperature range of from about −40° C. to about 100° C.

7. The process of claim 1, wherein the molar ratio of the isoparaffin to the olefin is from about 5:1 to about 25:1.

8. The process of claim 1, wherein the isoparaffin is isobutane and the olefin feed is a mixture of propylene and butenes.

9. The process of claim 1, wherein the isoparaffin is isobutane and the olefin feed is a mixture of butenes.

10. The process of claim 1, wherein the water and/or water-producing material is preintroduced into the catalyst.

11. The process of claim 1, wherein the water and/or water-producing material is cofed with the reactants.

12. The process of claim 10, wherein the amount of water preintroduced into the catalyst ranges from about 0.5 to about 25 percent by weight of the catalyst.

13. The process of claim 10, wherein the amount of water preintroduced into the catalyst ranges from about 1.0 to about 10 percent by weight of the catalyst.

14. The process of claim 11, wherein the amount of water ranges from about 0.1 ppmw to about 1 weight percent based upon the total hydrocarbon feed rate.

15. The process of claim 11, wherein the amount of water ranges from about 0.1 ppmw to about 500 ppmw based upon the total hydrocarbon feed rate.

16. The process of claim 1, wherein unconverted alpha olefins from the isomerization step are separated from isomerization effluent.

17. The process of claim 16, wherein the unconverted alpha olefin is 1-butene.

18. The process of claim 16, wherein the unconverted alpha olefins from the isomerization step are recycled back to the isomerization zone.

19. The process of claim 18, wherein the unconverted alpha olefin is 1-butene.

20. The process of claim 1, wherein the zeolite is selected from the group consisting of ZSM-3, ZSM-4, ZSM-12, ZSM-18, ZSM-20, zeolite Beta, zeolite L, mordenite, faujasite and zeolite Y.

21. The process of claim 1, wherein the zeolite is zeolite Beta.

22. The process of claim 1, wherein the zeolite is contained in a matrix.

23. The process of claim 1, wherein the weight hourly space velocity of that olefin is from about 0.01 to about 100.

24. The process of claim 1, wherein water is added intermittently to the reaction.

25. The process of claim 1, wherein the Lewis acid is maintained at a level in excess of that required to saturate the solid catalyst.

* * * * *